(12) United States Patent
Shroff et al.

(10) Patent No.: US 8,815,773 B2
(45) Date of Patent: Aug. 26, 2014

(54) HERBICIDAL COMBINATION

(75) Inventors: Jaidev Rajnikant Shroff, Mumbai (IN); Vikram Rajnikant Shroff, Mumbai (IN); Prakash Mahadev Jadhav, Mumbai (IN); Ashim Kumar Dutta, Mumbai (IN)

(73) Assignee: UPL Limited, Mumbai Maharashtra (IN)

( * ) Notice: Subject to any disclaimer, the term of this patent is extended or adjusted under 35 U.S.C. 154(b) by 242 days.

(21) Appl. No.: 12/845,861

(22) Filed: Jul. 29, 2010

(65) Prior Publication Data

US 2011/0028323 A1    Feb. 3, 2011

(30) Foreign Application Priority Data

Jul. 29, 2009 (IN) .......................... 1734/MUM/2009

(51) Int. Cl.
*A01N 57/04* (2006.01)
*A01P 13/00* (2006.01)
*A01N 41/06* (2006.01)

(52) U.S. Cl.
CPC ..................................... *A01N 41/06* (2013.01)
USPC ....................................................... 504/127

(58) Field of Classification Search
None
See application file for complete search history.

(56) References Cited

U.S. PATENT DOCUMENTS

| | | | |
|---|---|---|---|
| 5,118,338 A | 6/1992 | Moller | |
| 5,552,462 A * | 9/1996 | Yeh | 524/55 |
| 6,451,731 B1 * | 9/2002 | Agbaje et al. | 504/118 |
| 2003/0050194 A1 | 3/2003 | Hopkinson | |

FOREIGN PATENT DOCUMENTS

| | | |
|---|---|---|
| EP | 206537 | 12/1986 |
| EP | 0376910 | 7/1990 |
| GB | 2131327 | 6/1984 |
| WO | 97 31535 | 9/1997 |
| WO | 01/22814 A1 | 4/2001 |
| WO | 02/078442 A2 | 10/2002 |
| WO | 03/26429 | 4/2003 |
| WO | 2010/036996 A2 | 4/2010 |

OTHER PUBLICATIONS

Franz, J.E., "General Properties of Glyphosate and Glyphosate Salt", ACS Monograph 189, American Chemical Society, Washington DC, 1997, pp. 27-64.

Volgas G, Roberts J, Wayland M and Alford B, "A Unique Formulation of Glyphosate in the Acid Form", Journal of ASTM International, vol. 5, Issue 4, Apr. 2008.

Turner, DJ and Tabbush, PM, "Studies with Alternative Glyphosate Formulations", BCPC Monogram No. 28, 1985.

Horsley, Stephen B., "Control of Grass and Sedge in Allegheny Hardwood Stands with Roundup-Residual Herbicide Tank Mixes", Northern Journal of Applied Forestry, vol. 7, No. 3, Sep. 1990, pp. 124-129.

* cited by examiner

*Primary Examiner* — Abigail Fisher
*Assistant Examiner* — Daniel L Branson
(74) *Attorney, Agent, or Firm* — Merchant & Gould P.C.

(57) ABSTRACT

A herbicidal suspension concentrate formulation comprising effective amount of glyphosate acid, effective amount of oryzalin and polyalkylene oxides and their copolymers such as EO/PO copolymer. Also disclosed is a process for the preparation of the herbicidal suspension concentrate formulations according to the present invention.

27 Claims, No Drawings

US 8,815,773 B2

HERBICIDAL COMBINATION

FIELD OF INVENTION

The present invention relates to a suspension concentrate formulation comprising glyphosate acid in combination with oryzalin. More particularly, the present invention relates to a storage stable suspension concentrate comprising glyphosate acid and oryzalin.

BACKGROUND AND PRIOR ART

N-(Phosphonomethyl)glycine, also known by its common name glyphosate, is a widely-used broad spectrum post-emergent herbicide used to control the growth and proliferation of undesired plants. Typically it is applied to the foliage of the target plant, whereafter it is absorbed by the foliar tissue and translocated throughout the plant. Glyphosate is conventionally applied as an aqueous composition of a more water soluble salt form thereof. Commercially available formulations of glyphosate contain glyphosate in the form of any of its agriculturally acceptable salt in aqueous solution. However, the range of N-(Phosphonomethyl)glycine salts useful for controlling weeds is very broad (J. E. Franz et al., Glyphosate: A Unique Global Herbicide, ACS Monograph 189, American Chemical Society, Washington, D.C., 1997, pp. 27-64, herein incorporated by reference). However, glyphosate free acid form per se is relatively insoluble in water, it is usually formulated as any of its water soluble salt.

The article entitled "A unique formulation of glyphosate in the acid form", Volgas G, Roberts J, Wayland M and Alford B, Journal of ASTM International, Volume 5, Issue 4 relates to a formulation comprising glyphosate acid. This article teaches a disadvantage associated with these known glyphosate-salt formulations is that they need substantial amount of surfactants to enhance their uptake. It has been believed that the formulations including glyphosate free acid form would not need to rely on reduced surface tension or other surfactant effects to provide excellent uptake and herbicide efficacy. For example, in known 41 SL formulations of glyphosate isopropylamine salt, about 15% or more of amine ethoxylate surfactants are used, which is clearly undesirable.

Moreover, it has been found by the present inventors that the known formulations comprising glyphosate salt in combination with other active ingredients suffer from very poor suspensibility and are known to often fail the wet sieve test. These products display a considerable amount of sedimentation with time, often forming hard rock type lumps at the bottom of the storage containers. The increased sedimentation further aggravates the problem of nozzle clogging during the spraying application by a farmer. It is observed that when such a formulation is prepared as a diluted liquid or a solution to be sprayed, the same does not remain sprayable after the passage of a certain amount of time because of the high insoluble content. This can sometimes lead to a farmer rejecting an otherwise good product, which is certainly undesirable.

The present inventors attempted mixing an existing pendimethalin 40 SC formulation with a 41% glyphosate isopropylamine salt SL formulation in a 1:1 ratio to obtain a 20:20 product. This pre-mix displayed a suspensibility of 23% and heavy retention of particles on 500 BSS sieve. It was concluded that glyphosate salt would be mutually incompatible with other dinitroaniline herbicides as well apart from pendimethalin, such as oryzalin.

It was further found that the formulations hitherto known in the art comprising a glyphosate salt with oryzalin were retained by about 30-50% on a wet screen #150. It is thus desirable to develop a suspension concentrate formulation comprising glyphosate in a suitable form, wherein the formulation solves the problem of clogging associated with the conventional formulation and preferably, displays at most from about 0% to about 10% retention on standard wet sieve analysis.

Further, most of the known processes for the preparation of glyphosate which are described in the literature involve the separation of glyphosate in its acid form, which is converted to a desired salt form prior to being formulated. Accordingly, a formulation that includes glyphosate in its acid form would eliminate the need for it to be converted to its desired salt form prior to being formulated, which is desirable.

A formulation comprising glyphosate acid is mentioned in BCPC Monogram No. 28, 1985, by D J Turner and P M Tabbush. However, this disclosure teaches heating the glyphosate acid at 100° C. for about an hour with an excess of a fatty amine in water, during which process the glyphosate acid present in the formulation is converted to its salt form.

EP 206,537 describes a solid formulation comprising glyphosate derivatives. This formulation is taught to be prepared by melting a surfactant and adding the glyphosate compound in a solvent to the concentrated solution. The solvent is thereafter removed. However, this publication does not exemplify a formulation comprising glyphosate free acid.

U.S. Pat. No. 5,118,338 describes a water soluble powdery or granular free flowing formulation comprising glyphosate free acid and a specified surfactant. However, the solid formulations are known to have some inherent disadvantages. It is often desirable to present a herbicide in a concentrate form, which may be mixed with water before spray to form an emulsion spray. Moreover, it is also desirable to present a formulation having a high herbicide component, which is not always possible with a solid formulation.

It is known that suspension concentrate formulation provide these benefits as it comprises a water-based particulate suspension which contains no solvent. The microscopic particles of the herbicide remain on the applied surface for easy penetration and the lack of a solvent ensures no staining or odor problems.

It is therefore desirable to present a suspension concentrate formulation comprising glyphosate in its free acid form thereby overcoming the need to incorporate substantial amount of surfactants without compromising the herbicidal efficacy of the formulation.

Certain sulfanilamides are known selective pre-emergence herbicides, effective against many weeds. One such sulfanilamide is 4-(dipropylamino)-3,5-dinitrobenzenesulfonamide, commonly known as oryzalin. Oryzalin is a selective preemergence surface-applied herbicide used for control of annual grasses and broadleaf weeds in fruit trees, nut trees, vineyards, established bermudagrass turf and established ornamentals.

British Patent Specification No. 2,131,327 disclosed spray equipment useful for rotary dispensation of herbicides. Difficulties are encountered in obtaining a uniform spray when known spray mixtures of N-phosphonomethyglycine and sulfanilamide herbicides are employed using a device designed to discharge a herbicidal mixture from a distribution element by centrifugal force.

PCT application, WO 1997/031535 A1, discloses a synergistic combination of N-phosphonomethylglycine ester or acid adduct of an ester and oryzalin.

European patent, EP0376910 discloses an herbicidal aqueous composition comprising N-phosphonomethyglycine, a sulfanilamide herbicide and a polymeric thickening agent in an amount sufficient to thicken the composition such that at 25° C. the time elapsed for 100 ml of the composition to pass through the measurement orifice of a Ford B2 Cup is in the range of about 20-150 seconds. The composition was delivered to a target area using the rotary spray device disclosed in British Patent Specification No. 2,131,327. The experimental procedures exemplified in EP'910 were attempted by the present inventors. It was found that the resultant formulations demonstrated poor suspensibility (%) and failed the wet sieve test. Consequently, nozzle choking during the spray application was also observed. Moreover, none of the examples teach a suspension concentrate formulation including glyphosate in its free acid form. It is further often seen that for active ingredients that are formulated as suspension concentrates and which are denser than water tend to settle in the packaged product, which is undesirable.

It has thus been found that when glyphosate isopropylammonium salt is combined with oryzalin, it causes instant sedimentation and thus makes it unsuitable for spray application as the physical system loses its homogeneity and it blocks the spray nozzle. Another disadvantage of formulations comprising glyphosate in its salt form is the need to use a higher amount of surfactant, which is clearly undesirable.

PCT Publication No. WO 03/026429, which is incorporated herein by reference in its entirety, discloses compositions comprising suspension concentrates containing glyphosate acid and methods of preparing such suspension concentrates. However, this publication does not contemplate combination of glyphosate acid with other herbicides, particularly with dinitroaniline herbicides and more particularly with oryzalin. This publication therefore does not contemplate the problem of mutual physical incompatibility between glyphosate and oryzalin, which the present invention sets out to solve.

It is thus desirable to present a storage stable suspension concentrate formulation comprising a combination of glyphosate in its free acid form in addition to oryzalin, which is an unmet need in the art.

OBJECTIVES OF THE INVENTION

It is thus an object of the present invention is to provide a storage stable suspension concentrate formulation comprising glyphosate acid in combination with oryzalin.

Yet another object of the present invention is to provide a storage stable suspension concentrate formulation comprising glyphosate acid in combination with oryzalin wherein the formulation exhibits desirable suspensibility and passes the wet sieve test.

Yet another object of the present invention is to provide a storage stable suspension concentrate formulation comprising glyphosate acid in combination with oryzalin wherein said formulation does not cause nozzle choking thereby rendering the formulation suitable for spray applications even after the passage of a predetermined amount of time.

Yet another object of the present invention is to provide a storage stable suspension concentrate formulation comprising glyphosate acid in combination with oryzalin wherein said formulation exhibits at most from about 0% to about 10% retention (wet screen #150) on standard wet sieve analysis.

Another object of the present invention is to provide a storage stable suspension concentrate formulation comprising glyphosate acid in combination with oryzalin, which eliminates the need for glyphosate acid to be converted to its salt form prior to being formulated.

Yet another object of the present invention is to provide a storage stable suspension concentrate formulation comprising glyphosate acid in combination with oryzalin, wherein the formulation is free of an organic solvent.

Yet another object of the present invention is to provide a storage stable suspension concentrate formulation containing a substantially reduced amount of surfactants without compromising the uptake and herbicidal efficacy of the formulation.

The remaining portion of the description and claims meets at least one of these and other objectives.

SUMMARY OF THE PROPOSED INVENTION

Thus, in one aspect, the present invention provides a storage stable suspension concentrate formulation comprising (a) a herbicidally effective amount of glyphosate acid; and (b) a herbicidally effective amount of oryzalin.

In yet another aspect, the present invention provides a storage stable suspension concentrate formulation comprising:

(a) a herbicidally effective amount of glyphosate acid;
(b) a herbicidally effective amount of oryzalin; and
(c) at least one of an agrochemical adjuvant selected from an anti-freezing agent, an anti-caking agent, a surfactant, a thickener, an anti-foaming agent, a biocide and a filler.

In another aspect, the present invention provides a process for the preparation of a storage stable suspension concentrate formulation, said process comprising:

(a) mixing and homogenizing a plurality of agrochemical adjuvants selected from an anti-freezing agent, an anti-caking agent, a surfactant, an anti-foaming agent, a biocide and a filler;
(b) adding herbicidally effective amounts of glyphosate acid and oryzalin to the homogenous mixture of step (a) with constant stirring to obtain a slurry;
(c) micronizing the resultant slurry in a provided milling device; and
(d) adding predetermined amount of a thickener to obtain the resultant suspension concentrate formulation.

DESCRIPTION OF INVENTION

N-phosphonomethylglycine (glyphosate) is an organophosphorus, non-selective systemic herbicide. It is absorbed through the leaves, injected into the bole, or applied to the stump of a tree. Glyphosate is effective in killing a wide variety of plants, including grasses, broadleaf, and woody plants. It is generally used to kill weeds, especially perennials and broadcast or used in the cut-stump treatment as a forestry herbicide.

Sulfanilamide herbicide, oryzalin, is a selective pre-emergence surface applied herbicide used for control of annual grasses and broadleaf weeds in fruit trees, nut trees, vineyards and established ornamentals.

It has been surprisingly found that a suspension concentrate formulation comprising glyphosate acid in combination with oryzalin is unexpectedly storage stable and exhibits desirable suspensibility and passes the wet sieve test.

Thus, in an aspect, the present invention provides a storage stable suspension concentrate formulation comprising (a) a herbicidally effective amount of glyphosate acid; and (b) a herbicidally effective amount of oryzalin.

Preferably, the storage stable composition in this aspect of the present invention further comprises an agrochemical adjuvant selected from an anti-freezing agent, an anti-caking agent, a surfactant, a thickener, an anti-foaming agent, a biocide and a filler.

Thus, in another aspect, the present invention provides a storage stable suspension concentrate formulation comprising:
(a) a herbicidally effective amount of glyphosate acid;
(b) a herbicidally effective amount of oryzalin; and
(c) at least one of an agrochemical adjuvant selected from an anti-freezing agent, an anti-caking agent, a surfactant, a thickener, an anti-foaming agent, a biocide and a filler.

It has been found that the formulations according to the present invention exhibit good suspensibility and do not undergo sedimentation and thus remains sprayable even after the passage of a considerable amount of time. The present formulations therefore do not cause any nozzle clogging during the spray application by a farmer. Surprisingly, it has been found that the storage stable suspension concentrate formulations according to the present invention exhibit at most from about 0% to about 10% retention (wet screen #150) on standard wet sieve analysis.

The term "agrochemically effective amount" of either glyphosate acid or oryzalin is that quantity of glyphosate acid or oryzalin which when applied in any amount will provide the required control of broad leaved weeds and grasses. The particular amount is dependent upon many factors including, for example, the crop, weeds sought to be controlled and environmental conditions. The selection of the proper quantity of active agent to be applied, however, is within the expertise of one skilled in the art and is not considered particularly limiting.

However, in a preferred embodiment, oryzalin may be present in an amount of 2% to about 40% by total weight of the formulation. In another embodiment, glyphosate acid may be present in an amount of 2% to about 50% by total weight of the formulation.

Thus, the present invention provides a suspension concentrate formulation comprising glyphosate acid in combination with oryzalin. Practically, a good product was expected when glyphosate salt was mixed with known oryzalin SC formulation. But on the contrary, when oryzalin SC was mixed with commercially available glyphosate SL and SG formulations, the end product showed very poor suspensibility and failed the wet sieve test. It was also found that any formulation comprising glyphosate isopropylammonium salt with oryzalin demonstrated problem of suspensibility as a susposolution or as a wettable/water dispersible powder.

It was surprisingly found that a suspension concentrate formulation comprising glyphosate acid and preferably an herbicidally effective amount of oryzalin demonstrated surprisingly superior suspensibility and regularly passed the wet sieve test. It was further additionally found that glyphosate in its free acid form is much more biologically active than any glyphosate salt so the formulations according to the present invention resulted in a better bioactivity with a lesser dosage of application. It was also found that the formulations according to the present invention simultaneously also solved the problem of nozzle choking frequently encountered during the application of glyphosate and oryzalin tank mixes.

Moreover, the problem of sedimentation and poor storage stability of oryzalin-glyphosate salt combination arising due to the mutual incompatibility between oryzalin and glyphosate salt was also seen to be solved by the storage stable suspension concentrate formulations according to the present invention.

In another aspect, the present invention provides a process for the preparation of a storage stable suspension concentrate formulation, said process comprising:
(a) mixing and homogenizing a plurality of agrochemical adjuvants selected from an anti-freezing agent, an anti-caking agent, a surfactant, an anti-foaming agent, a biocide and a filler;
(b) adding herbicidally effective amounts of glyphosate acid and oryzalin to the homogenous mixture of step (a) with constant stirring to obtain a slurry;
(c) micronizing the resultant slurry in a provided milling device; and
(d) adding predetermined amount of a thickener to obtain the resultant suspension concentrate formulation.

Preferably, the formulations according to the present invention may comprise at least or several of the agrochemical adjuvants that are known in the art. Such adjuvants may preferably be selected from an anti-freezing agent, anti-caking agent, a surfactant or mixtures thereof, a thickener, an anti-foaming agent, a biocide and a filler.

Preferably, the anti-freezing agent includes a compound selected from urea, methanol, ethylene glycol and propylene glycol though other anti-freezing agents are not excluded. Preferably, the anti-freezing agent may be present in an amount of about 0.2% to about 10% by total weight of the formulation.

The anti-caking agent are typically used to prevent clumping of the formulation and may be selected from sodium and ammonium phosphates; sodium acetate; sodium metasilicate; magnesium, zinc and calcium sulfate; magnesium hydroxide; anhydrous calcium chloride; sodium alkylsulfosuccinates; calcium and barium oxides; and precipitated silica. Preferably, the anti-caking agent according to an embodiment of the present invention is precipitated silica.

In this embodiment, the anti-caking agent may be used in an amount upto about 2.0% by total weight of the formulation.

The formulations according to the present invention preferably include at least one surfactant. Preferably, the formulations according to the present invention include a mixture of surfactants which may function as a dispersant and/or a wetting agent.

The preferred surfactant may be water soluble or water insoluble and may be selected from sodium, calcium and ammonium salts of ligninsulfonates which may be optionally polyethoxylated; salts of maleic anhydride copolymers, salts of polyacrylic acids; salts of condensed phenolsulfonic acids; salts of the naphthalene sulfonate-formaldehyde condensates; polyvinylpyrrolidone; polyvinyl alcohol; polyalkylene oxides and their copolymers such as EO/PO copolymer.

In another embodiment, the surfactant may also be selected from alkyl sulfosuccinates and taurates; alkyl sulfates and phosphate esters; acetylenic diols; ethoxyfluorinated alcohols; ethoxylated silicones and alkyl phenol ethoxylates; alcohol ethoxylates and organic sulfonates.

In a preferred embodiment, it was found that physical incompatibility between glyphosate acid and oryzalin was substantially reduced to afford a surprisingly stable formulation according to the present invention in the presence of a non-ionic surfactant comprising polyalkylene oxides and their copolymers such as EO/PO copolymer. It was found that polyalkylene oxides and their copolymers such as EO/PO copolymer particularly facilitated the handling ease of the formulations according to the present invention.

In this embodiment, the surfactant or mixtures thereof may be used in an amount of about 0.2% to about 30% by total weight of the formulation. Still more preferably, the formulations according to the present invention comprise a surfactant, preferably polyalkylene oxides and their copolymers such as EO/PO copolymer, in an amount of about 3% to about 6%, more preferably about 3% by total weight of the formulation.

Therefore, in this embodiment, the present invention provides a suspension concentrate having a reduced amount of the surfactant required without compromising the uptake and consequent herbicidal activity of the herbicides present within the formulations of the present invention.

It is therefore desirable to present a suspension concentrate formulation comprising glyphosate in its free acid form thereby overcoming the need to incorporate substantial amount of surfactants without compromising the herbicidal efficacy of the formulation.

The compositions according to the present invention preferably include at least a thickener. The thickener according to the present invention may be selected from a heteropolysaccharide or a synthetic or natural gum. The said gum may preferably be in the form of a gel of predetermined strengths such as 2 percent.

In this embodiment, the thickener may be present in an amount of about 1% to about 15% by total weight of the formulation.

The formulations according to the present invention may further include at least one anti-foaming agent. The anti-foaming agent included within the formulations of the present invention may be selected from but are not limited to stearates; silicones; dimethyl polysiloxanes and ethoxylates having HLB values less than 5. Preferably, the anti-foaming agent is dimethyl polysiloxanes or a silicone based defoamer.

In an embodiment, the anti-foaming agent may be present within the formulations according to the present invention in an amount of about 0.1% to about 5% by total weight of the formulation.

Preferably, the formulations of the present invention further include a biocide, which may be a mixture comprising dipropylene glycol, 1,2-bezisothiazolin-3-one, sodium hydroxide and water. However, it should be understood that the present invention is not limited to these specific biocides and other biocides that are known in the art may also be conveniently used.

In an embodiment, the biocide may be present within the formulations according to the present invention in an amount of about 0.01% to about 1.0% by total weight of the formulation.

The formulations of the present invention may optionally comprise a filler, which in a preferred embodiment of the present invention may be distilled water.

The formulations may optionally comprise one or more stabilizers and/or diluents that are conventionally known in the art to be used in such formulations.

Suitable diluents include but are not limited to sulfates of sodium, potassium, magnesium and zinc; sodium and potassium chloride; gelatin; urea; sugar; sorbitol; sodium benzoate; lactose; alkali metal phosphates; alkaline earth metal phosphates; starch or modified starch; cyclodextrin; aluminum, calcium and zinc oxide; calcium and magnesium carbonate and sodium, potassium, calcium and barium sulfate.

In an embodiment, the storage stable suspension concentrate formulations of the present invention comprise glyphosate acid and oryzalin in any preferred weight ratio. Still more preferably, glyphosate acid and oryzalin are included within the present formulations in a preferable weight ratio of 24:24, which was found to possess good efficacy on the desired weeds.

In yet another embodiment, the suspension concentrate formulations according to the present invention comprises 120 g/L of glyphosate acid and 240 g/L of oryzalin.

In yet another embodiment, the storage stable suspension concentrate formulations of the present invention comprise glyphosate acid and oryzalin in a preferable weight ratio of about 36:12, which was further found to possess good efficacy on the desired weeds.

In another embodiment, the formulations according to the present invention comprised glyphosate acid and oryzalin in their recommended and/or desired dosage rates depending on the respective end uses. For example, the desired dosage rate for oryzalin varied from 3-4 pounds per gallon for nursery and ornamental uses while it varied from 4-5 pounds per gallon for tree and vine drops. On the other hand, the desired rate for glyphosate acid was 1-1.5 pound per gallon for nursery, ornamentals, tree and vine crops while it was about 0.28 and 0.375 pounds for annual weed control and perennial weed control respectively. The rate calculations were done based on the percentage concentrations of the herbicidal compound based on grams per liter of the active ingredient. For example, 12% of the herbicidal compounds of the present invention i.e. 120 g/L corresponded to 1 pound per gallon of the present formulations.

In this embodiment, it was found that the desired dosage of glyphosate acid and oryzalin were met at 12% glyphosate acid and 36% oryzalin in the formulation respectively. In this embodiment, the desired range of oryzalin dosage varied from 3.0 to 5.0 pounds per gallon of the formulation while the desired dosage of glyphosate acid varied from 1.0 to 1.7 pound per gallon of the formulations according to the present invention.

Exemplary formulation according to this and other aspects and embodiments of the present invention were prepared as hereunder. The invention shall now be described with reference to the following specific examples. It should be noted that the example(s) appended below illustrate rather than limit the invention, and that those skilled in the art will be able to design many alternative embodiments without departing from the scope of the present invention.

Example 1

| S No. | Component | Percentage (w/w) |
|---|---|---|
| 1 | Glyphosate acid (95%) | 10.53 |
| 2 | Oryzalin (95%) | 32.63 |
| 3 | Alkyl EO/PO Copolymer | 3.00 |
| 4 | Silicone Oil emulsion (SAG 1572) | 1.00 |
| 5 | Precipitated silica | 1.00 |
| 6 | Propylene glycol | 7.00 |
| 7 | Proxel GXL | 0.10 |
| 8 | Rhodopol 23 (2% gel) | 12.00 |
| 9 | Demineralized water | QS |

Table 1 below summarizes the stability results for the formulation of example 1 above. It was indeed surprising that desirable formulation characteristics were achieved despite the formulation comprising only 3% of a surfactant, which was unexpected for the glyphosate-containing formulation.

Example 2

| Sr. No. | | % (w/w) |
|---|---|---|
| 1. | Glyphosate acid technical (active) | 24.00 |
| 2. | Oryzalin technical (active) | 24.00 |
| 3. | Urea (Antifreeze agent) | 6.00 |
| 4. | Precipitated silica(Anticaking agent) | 0.50 |
| 5. | Alkyl EO/PO copolymer(Surfactant) | 3.00 |
| 6. | Heteropoly saccharide(Thickener) | 2.50 |
| 7. | Silicone defoamer(Antifoaming agent) | 1.00 |
| 8. | [Dipropylene glycol + 1,2-Benzisothia-zolin-3-one + Sodium hydroxide + water] (Biocide) | 0.10 |
| 9. | Distilled water(Filler) | QS to 100 |

Table 2 below displays the stability results for the formulation exemplified in example 2 above. It was indeed surprising that desirable formulation characteristics were achieved despite the formulation comprising only 3% of a surfactant, which was unexpected for the glyphosate-containing formulation.

TABLE 2

| Sr. No | Parameter | 0 day stability | 14 d/54° C. stability | 7 d/0 ± 2° C. stability |
|---|---|---|---|---|
| 1 | % a.i, Glyphosate acid | 25.84 | 25.78 | 25.73 |
| 2 | % a.i Oryzalin | 25.12 | 25.19 | 25.47 |
| 3 | % Suspensibility, Glyphosate acid (% w/w, active basis) | 101.90 | 102.42 | 101.48 |
| 4 | % Suspensibility, Oryzalin (% w/w, active basis) | 98.37 | 96.29 | 97.28 |
| 5 | pH (1% Aq. Solution) | 1.69 | 1.70 | 1.68 |
| 6 | Persistant foaming (ml after 1 min) | 10 ml | 10 ml | 10 ml |
| 7 | Particle size analysis | 90% = 6.03 micron | 90% = 7.17 micron | 90% = 6 micron |
| 8 | Wet sieve test (500 BSS/25 micron) | No residue | No residue | No residue |
| 9 | Hard water suspensibility (1000 ppm) | 98.18 | 100.18 | 100.17 |
| 10 | Stability of physical system | Stable | No caking | No caking |

TABLE 1

| Parameters | AMB | 5 Months | 14 d 54 ± 2° C. AHS + 5 month RT |
|---|---|---|---|
| pH of 1% Suspension (D/W: 6.3) | 2.59 | 2.80 | 2.81 |
| Suspensibility (500 PPM) gravimetric At 20° C. | 104.22 | 101.98 | 102.54 |
| Wet Sieve (350 BSS) | 0.1 | 0.1 | 0.1 |
| Persistent foam | Nil | Nil | Nil |
| Density (Hydrometer) | 1.18 gm/cc | 1.18 | 1.18 |
| Sp Gr. at 20° C. | 1.085 | | |
| Viscosity Sp: 63 T: 25 ± 2° C. RPM/Torque/η 10 | 24-2915 | 12-1548 | 9-1044 |
| 50 | 41-1001 | 25-626 | 19.5-460 |
| 100 | 51-614 | 34-405 | 28-313 |
| 200 | 66-398 | 45-274 | 35-209 |
| 250 | 72-344 | 50-240 | 40-188 |
| Particle size data D (0.1) | 0.66 | 0.679 | 0.785 |
| D (0.5) | 2.874 | 2.638 | 3.253 |
| D (0.9) | 8.895 | 9.238 | 8.680 |
| Stability of physical system | Stable | No caking | No caking |

Example 3

| Sr. No. | Ingredient | % (w/w) |
|---|---|---|
| 1. | Glyphosate acid technical (active) | 25.82 |
| 2. | Oryzalin technical (active) | 25.76 |
| 3. | Tensiofix (Surfactant) | 3.45 |
| 4. | Dimethyl polysiloxane (Defoamer) | 0.70 |
| 5. | Gum (2% gel) (Biocide) | 5.00 |
| 6. | [Dipropylene glycol + 1,2-Benzisothiazolin-3-one + Sodium hydroxide + water] (Biocide) | 0.18 |
| 7. | Sulfonated aromatic polymer, sodium salt (Surfactant) | 1.18 |
| 8. | di-ol (Antifreeze agent) | 5.75 |
| 9. | Distilled water (Filler) | QS to 100 |

Table 3 below displays the stability results for the formulation exemplified under the example 3 provided above. It was indeed surprising that desirable formulation characteristics were achieved despite the formulation comprising only 4.63% of a surfactant, which was unexpected for the glyphosate-containing formulation, which are known to conventionally comprise greater than 30% by weight of the formulation of a surfactant.

TABLE 3

| No. | Parameter | 0 day stability | 14 d I 54° C. stability | 7 d/0 ± 2° C. stability |
|---|---|---|---|---|
| 1 | % a.i, Glyphosate acid | 25.84 | 25.78 | 25.73 |
| 2 | % a.i Oryzalin | 25.12 | 25.19 | 25.47 |
| 3 | % Suspensibility, Glyphosate acid (% w/w, active basis) | 101.90 | 102.42 | 101.48 |
| 4 | % Suspensibility, Oryzalin (% w/w, active basis) | 98.37 | 96.29 | 97.28 |
| 5 | pH (1% Aq. Solution) | 1.69 | 1.70 | 1.68 |
| 6 | Persistant foaming (ml after 1 min) | 10 ml | 10 ml | 10 ml |
| 7 | Particle size analysis | 90% = 6.03 micron | 90% = 7.17 micron | 90% = 6 micron |
| 8 | Wet sieve test (500 BSS/25 micron) | No residue | No residue | No residue |
| 9 | Hard water suspensibility (1000 ppm) | 98.18 | 100.18 | 100.17 |
| 10 | Stability of physical system | Stable | No caking | No caking |

Example 4

| Sr. No. | Ingredient | % (w/w) |
|---|---|---|
| 1. | Glyphosate acid technical (active) | 32.63 |
| 2. | Oryzalin technical (active) | 7.94 |
| 3. | Alkyl EO/PO copolymer (Surfactant) | 3.00 |
| 4. | Sodium lignosulfonate (Surfactant) | 2.40 |
| 5. | Ammonium ligno sulfonate (Surfactant) | 0.60 |
| 6. | Silicone defoamer (Antifoaming agent) | 1.00 |
| 7. | Gum (2% gel) (thickening agent) | 3.00 |
| 8. | [Dipropylene glycol + 1,2-Benzisothiazolin-3-one + Sodium hydroxide + water] (Biocide) | 0.10 |
| 9. | di-ol (Antifreeze agent) | 8.00 |
| 10. | Precipitated silica (Anticaking agent) | 1.00 |
| 11. | Distilled water (Filler) | QS to 100 |

Table 4 below shows the stability results for the formulation exemplified under example 4 above. It was indeed surprising that desirable formulation characteristics were achieved despite the formulation comprising only 6% of a surfactant, which was unexpected for the glyphosate-containing formulation, which are known to conventionally comprise greater than 30% by weight of the formulation of a surfactant.

TABLE 4

| Sr No. | Parameter | 0 day stability | 14 d/54° C. stability | 7 d/ 0 ± 2° C. stability |
|---|---|---|---|---|
| 1 | % a.i, Glyphosate acid | 7.58 | 7.84 | 7.52 |
| 2 | % a.i Oryzalin | 31.84 | 31.75 | 31.54 |
| 3 | % Suspensibility, Glyphosate acid (% w/w, active basis) | 99.85 | 99.52 | 99.47 |
| 4 | % Suspensibility, Oryzalin (% w/w, active basis) | 101.8 | 102.4 | 100.8 |
| 5 | pH (1% Aq. Solution) | 1.61 | 1.67 | 1.60 |
| 6 | Persistant foaming (ml after 1 min) | Nil | Nil | Nil |
| 7 | Particle size analysis | 90% = 9.58 micron | 90% = 9.47 micron | 90% = 9.62 micron |
| 8 | Wet sieve test (500 BSS/25 micron) | No residue | No residue | No residue |
| 9 | Stability of physical system | Stable | No caking | No caking |

The present invention thus enables a pre-mix formulation of oryzalin and glyphosate acid. Table 5 below demonstrates the advantages of the pre-mix formulations according to the present invention.

TABLE 5

| Parameter | Glyphosate | Oryzalin | Glyphosate + Oryzalin |
|---|---|---|---|
| Dose (a.i./acre) | 1500 | 725 | 480 + 480 |
| Spectrum of weed | Perennial, Annual, Broad leaved | Broadleaved | Broader spectrum |
| Crop | Fruits, soybean, maize, Total Killer | Fruits, Soybean, Maize, Total killer | Similar crop spectrum |
| Application timing | Pre crop emergence | Preemergence | Simultaneous application |

TABLE 5-continued

| Parameter | Glyphosate | Oryzalin | Glyphosate + Oryzalin |
|---|---|---|---|
| Mode of entry | Foliage | Foliage and root | Foliage and root |
| Mode of action | Protein biosynthesis | Cell division inhibition | Dual MOA Less resistance development |
| DT50 | Acid: 3 d Salt: 40 d | 80 d | Extended time period |

Example 5

The formulation appearing in the below table including 360 g/L glyphosate acid and 120 g/L oryzalin was prepared using the process described hereinbefore. This formulation was also found to possess good suspensibility and consistently passed the wet sieve test.

| S No. | Ingredient | Percentage (w/w) |
|---|---|---|
| 1 | Oryzalin technical | 10.72 |
| 2 | Glyphosate acid technical | 31.16 |
| 3 | Tergitol XD | 3.00 |
| 4 | Sodium lignosulfonate | 2.40 |
| 5 | Ammonium lignosulfonate | 0.60 |
| 6 | SAG 1572 (defoamer) | 1.00 |
| 7 | Gum (2% gel) | 3.00 |
| 8 | Proxel GXL | 0.10 |
| 9 | Propylene glycol | 8.00 |
| 10 | Precipitated Silica | 0.50 |
| 11 | Water | QS |

The present inventors attempted to replace the glyphosate acid component of the present formulations with a known glyphosate salt. It was found that the resultant formulation exhibited very poor suspensibility and also failed the wet sieve test. It was further found that such modified formulation caused heavy choking of the spray nozzle and was unsuitable for spray applications.

Table 6 below demonstrates the percentage suspensibility and wet sieve test result of the formulations according to the present invention wherein the glyphosate acid component of the formulation was replaced with glypshate IPA salt.

TABLE 6

| Parameter | 0 day | 14 d 54° C. Stability | 7 d 0 ± 2° C. stability |
|---|---|---|---|
| % a.i, Glyphosate IPA salt | 24.18 | 24.70 | 23.51 |
| % a.i Oryzalin | 12.18 | 12.01 | 12.45 |
| % Suspensibility | 18.74 | 13.71 | 17.58 |
| pH(1% aq.) | 6.74 | 6.81 | 6.18 |
| Persistant foaming (ml after 1 min) | 10 ml | 10 ml | 10 ml |
| Particle size analysis | 90% = 7.14 micron | 90% = 7.19 micron | 90% = 8.41 micron |
| Wet sieve test (500 BSS/25 micron) (% retension) | 27.12 | 30.18 | 25.47 |
| Stability of physical system | Stable | No caking | No caking |

Table 7 below exemplifies a suspo-solution formulation comprising glyphosate isopropylammonium salt in combination with oryzalin, wherein conventional thickeners, anti-foaming agent, surfactants, biocide and fillers were selected. The percentage suspensibility and wet sieve test was conducted on the so-obtained formulation set out below in table 6.

TABLE 7

| S No. | Component | % (w/w) | Function |
|---|---|---|---|
| 1 | Glyphosate iso-propylammonium salt (41% IPA) | 27.67 | Active ingredient |
| 2 | Oryzalin | 13.30 | Active ingredient |
| 3 | Rhodopol 23 gel (2% in water) | 7.50 | Thickener |
| 4 | Agnique DFM 111S | 0.10 | Anti-foam |
| 5 | Kaolin | 2.00 | Filler |
| 6 | Morwet EFW | 2.50 | Surfactant |
| 7 | Proxel GXL | 0.01 | Biocide |
| 8 | Water | 54.35 | Filler |

The tested formulation showed only 52.17% suspensibility and 12.14% residue on 200 BSS under the wet sieve test. The formulation therefore failed the wet sieve test and the suspensibility test and could cause nozzle choking. The pH of an 1% aqueous solution of the formulation was found to be 5.7. A 10 mL persistent foam was noted at 1 minute, while the residue was 2.10% in pourability test.

The stability parameters of the formulation according to Example 1 of the present invention were compared against the conventional formulation tested above containing glyphosate salt as hereunder:

| Parameter | Formulation of Example 1 of the present invention | Conventional formulation |
|---|---|---|
| pH | 2.60 | 5.70 |
| Suspensibility | 100% | 53% |
| Wet sieve | 0.1% | 12% |
| Physical stability after dilution in water | Uniform suspension | Heavy settling or agglomeration |

Thus, it was concluded that the formulations according to the present invention comprising glyphosate in its free acid form possesses surprisingly better suspensibility and very low wet sieve retention vis-à-vis formulations comprising a glyphosate salt under similar experimental conditions. The formulation according to the present invention formed an uniform suspension whereas heavy settling or agglomeration was observed in the conventional formulations. It was surprisingly found that the presence of glyphosate acid in combination with oryzalin stabilizes the suspension concentrate formulation apart from being the active ingredient of the formulation.

The invention has been described above with reference to the specific examples. It should be noted that the example(s) appended above illustrate rather than limit the invention, and that those skilled in the art will be able to design many alternative embodiments without departing from the scope of the appended claims. Other than in the operating examples provided hereinbefore or where otherwise indicated, all numbers expressing quantities of ingredients or reaction conditions are to be understood as being modified in all instances by the term "about".

We claim:

1. A composition comprising:
   about 5% to about 50% by weight glyphosate acid; and
   about 5% to about 40% by weight oryzalin,
   wherein the composition is storage stable suspension concentrate, exhibits at most from about 0% to about 10% retention on wet screen #150 on standard wet sieve analysis and has a viscosity measured at spindle number 63 at 25±2° C. less than about 1000 cps.

2. The composition of claim 1, further comprising at least one agrochemical adjuvant selected from an anti-freezing agent, an anti-caking agent, a surfactant, a thickener, an anti-foaming agent, a biocide, and a filler.

3. The composition of claim 2, comprising anti-freezing agent selected from urea, methanol, ethylene glycol, or propylene glycol in an amount of from about 0.2% to about 10% by weight.

4. The composition of claim 2, comprising anti-caking agent selected from sodium phosphate, ammonium phosphate, sodium acetate, sodium metasilicate, magnesium, zinc sulfate, calcium sulfate, magnesium hydroxide, anhydrous calcium chloride, sodium alkylsulfosuccinates, calcium oxide, barium oxide, and precipitated silica in an amount of up to about 2.0% by weight.

5. The composition of claim 4, comprising precipitated silica in an amount of up to about 2.0% by weight.

6. The composition of claim 2, comprising surfactant selected from sodium salt of ligninsulfonate, calcium salt of ligninsulfonate, and ammonium salt of ligninsulfonates, front sodium salt of polyoxyethylated ligninsulfonate, calcium salt of polyoxyethylated ligninsulfonate, and ammonium salt of polyoxyethylated ligninsulfonate, salt of a maleic anhydride copolymer, a salt of a polyacrylic acid, a salts of a condensed phenolsulfonic acids, a salt of a naphthalene sulfonate-formaldehyde condensate, polyvinylpyrrolidone, polyvinyl alcohol, polyalkylene oxide, a copolymer of a polyalkylene oxide, alkyl sulfosuccinates, alkyl taurate, alkyl sulfate, alkyl phosphate, acetylenic diols, ethoxyfluorinated alcohols, ethoxylated silicones, alkyl phenol ethoxylates, alcohol ethoxylates, and organic sulfonates.

7. The composition of claim 6, wherein said surfactant is present in an amount of about 0.2% to about 30% by weight.

8. The composition of claim 6, wherein said surfactant comprises a polyalkylene oxide or copolymer thereof.

9. The composition of claim 8, wherein said polyalkylene oxide or copolymer thereof is present in an amount of about 3% to about 6% by weight.

10. The composition of claim 2, comprising thickener selected from heteropolysaccharide, a synthetic, and a natural gum.

11. The composition of claim 10, wherein said synthetic or natural gum is in the form of a gel of predetermined strength of about 2 percent.

12. The composition of claim 10, wherein said thickener is present in an amount of about 1% to about 15% by weight.

13. The composition of claim 2, comprising anti-foaming agent selected from a stearate; a silicone; a dimethyl polysiloxane and an ethoxylate having HLB values, said anti-foaming agent being present in an amount of about 0.1% to about 5% by weight.

14. The composition of 13, wherein said anti-foaming agent comprises a dimethyl polysiloxane or a silicone based defoamer, said anti-foaming agent being present in an amount of about 0.1% to about 5% by weight.

15. The composition of claim 2, comprising biocide selected from dipropylene glycol, 1,2-bezisothiazolin-3-one, sodium hydroxide, water, and mixtures thereof in an amount of about 0.01% to about 1.0% by weight.

16. The composition of claim 1, further comprising a diluent selected from sodium sulfate, potassium sulfate, magnesium sulfate, zinc sulfate, sodium chloride, potassium chloride, gelatin, urea, sugar, sorbitol, sodium benzoate, lactose, alkali metal phosphate, alkaline earth metal phosphate, starch, modified starch, cyclodextrin, aluminum oxide, calcium oxide, zinc oxide, calcium carbonate, magnesium carbonate, calcium sulfate, and barium sulfate.

17. The composition of claim 1, comprising about 12% glyphosate acid and about 36% oryzalin.

18. A process for the preparation of the storage stable suspension concentrate of claim 1, said process comprising:
   mixing and homogenizing a plurality of agrochemical adjuvants selected from an anti-freezing agent, an anti-caking agent, a surfactant, an anti-foaming agent, a biocide and a filler;
   adding herbicidally effective amounts of glyphosate acid and oryzalin to the homogenous mixture with constant stirring to obtain a slurry;
   micronizing the resultant slurry in a provided milling device; and
   adding predetermined amount of a thickener to obtain the resultant suspension concentrate formulation.

19. The composition of claim 8, wherein the polyalkylene oxide or copolymer thereof comprises an EO/PO copolymer.

20. The composition of claim 9, wherein the polyalkylene oxide or copolymer thereof comprises an EO/PO copolymer.

21. The composition of claim 1 in the form of a suspension concentrate.

22. The composition of claim 1, comprising about 36% glyphosate acid and about 12% oryzalin.

23. The composition of claim 1, comprising about 24% glyphosate acid and about 24% oryzalin.

24. The composition of claim 6, wherein the copolymer of a polyalkylene oxide comprises an EO/PO copolymer.

25. A composition comprising:
   about 5% to about 50% by weight glyphosate acid; and
   about 5% to about 40% by weight oryzalin;
   up to about 2% by weight anticaking agent selected from the group consisting of sodium phosphate, ammonium phosphate, sodium acetate, sodium metasilicate, magnesium sulfate, zinc sulfate, calcium sulfate, magnesium hydroxide, anhydrous calcium chloride, sodium alkylsulfosuccinate, calcium oxide, barium oxide, and precipitated silica;
   wherein the composition is in the form of a storage stable suspension concentrate, exhibits at most from about 0% to about 10% retention on wet screen #150 on standard wet sieve analysis, and has a viscosity measured at spindle number 63 at 25±2° C. less than about 1000 cps.

26. The composition of claim 25, wherein the anticaking agent is precipitated silica.

27. A composition comprising:
   about 5% to about 50% by weight glyphosate acid; and
   about 5% to about 40% by weight oryzalin;
   up to about 2% by weight anticaking agent selected from the group consisting of sodium phosphate, ammonium phosphate, sodium acetate, sodium metasilicate, magnesium sulfate, zinc sulfate, calcium sulfite, magnesium hydroxide, anhydrous calcium chloride, sodium alkylsulfosuccinate, calcium oxide, barium oxide, and precipitated silica;
   about 0.2% to about 10% by weight an antifreezing agent selected from the group consisting of urea, methanol, ethylene glycol and propylene glycol;
   about 0.2% to about 30% by weight a surfactant selected from the group consisting of sodium salt of ligninsulfonate, calcium salt of ligninsulfonate, and ammonium salt of ligninsulfonate, from sodium salt of polyoxyethylated ligninsulfonate, calcium salt of polyoxyethylated ligninsulfonate, and ammonium salt of polyoxyethylated ligninsulfonate, a salt of a maleic anhydride copolymer, a salt of a polyacrylic acid; a salt of a condensed phenolsulfonic acid, a salt of a naphthalene sulfonate-formaldehyde condensate, polyvinylpyrrolidone, polyvinyl alcohol, polyalkylene oxide, a copolymer of a polyalkylene oxide, alkyl sulfosuccinate, alkyl taurate, alkyl sulfate, alkyl phosphate, acetylenic diols, ethoxyfluorinated alcohols, ethoxylated silicone, alkyl phenol ethoxylates, alcohol ethoxylates, and organic sulfone;

about 1% to about 15% by weight thickener selected from the group consisting of heteropolysaccharide, synthetic gum, and natural gum;

about 0.1% to about 5% by weight antifoaming agent selected from the group consisting of a stearate, a silicone, a dimethyl polysiloxane, and an ethoxylate;

about 0.1% to about 1% by weight a biocide, which is 1,2-benzisothiazolin-3-one in admixture with dipropylene glycol and sodium hydroxide;

at least one diluent selected from the group consisting of sodium sulfate, potassium sulfate, magnesium sulfate, zinc sulfate, sodium chloride, potassium chloride, gelatin, urea, sugar, sorbitol, sodium benzoate, lactose, alkali metal phosphate, alkaline earth metal phosphate, starch, modified starch, cyclodextrin, aluminum oxide, calcium oxide, zinc oxide, calcium carbonate, magnesium carbonate, calcium sulfate, and barium sulfate; and a filler, which is water;

wherein the composition is in the form of a storage stable suspension concentrate, exhibits at most from about 0% to about 10% retention on wet screen #150 on standard wet sieve analysis, and has a viscosity measured at spindle number 63 at 25±2° C. less than about 1000 cps.

* * * * *